US012277720B2

(12) United States Patent
Oda

(10) Patent No.: US 12,277,720 B2
(45) Date of Patent: Apr. 15, 2025

(54) INFORMATION PROCESSING DEVICE, INFORMATION PROCESSING METHOD, AND INFORMATION PROCESSING PROGRAM

(71) Applicant: FUJIFILM CORPORATION, Tokyo (JP)

(72) Inventor: Yoshinari Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 397 days.

(21) Appl. No.: 17/930,721

(22) Filed: Sep. 9, 2022

(65) Prior Publication Data
US 2023/0005168 A1    Jan. 5, 2023

Related U.S. Application Data

(63) Continuation of application No. PCT/JP2021/011504, filed on Mar. 19, 2021.

(30) Foreign Application Priority Data

Mar. 31, 2020 (JP) ................................. 2020-064479

(51) Int. Cl.
G06K 9/00      (2022.01)
G01S 17/894    (2020.01)
(Continued)

(52) U.S. Cl.
CPC ............ *G06T 7/521* (2017.01); *G01S 17/894* (2020.01); *G06T 7/60* (2013.01); *G06T 7/70* (2017.01);
(Continued)

(58) Field of Classification Search
CPC .. G06T 7/521; G06T 7/60; G06T 7/70; G06T 2207/10028; G06T 2207/10116;
(Continued)

(56) References Cited

U.S. PATENT DOCUMENTS 6,206,566 B1 *   3/2001  Schuetz ................. A61B 6/547
                                                              378/205
9,433,395 B2 *   9/2016  Kang ..................... A61B 6/544
(Continued)

FOREIGN PATENT DOCUMENTS

EP       2869264 A1 *   5/2015    ............. A63F 13/06
JP     2015-167603 A      9/2015
(Continued)

OTHER PUBLICATIONS

A Realistic X-Ray Simulation for C-Arm Geometry Calibration, Sabine Thurauf et al., IEEE, 2016, pp. 383-388 (Year: 2016).*
(Continued)

Primary Examiner — Jayesh A Patel
(74) Attorney, Agent, or Firm — SOLARIS Intellectual Property Group, PLLC

(57) ABSTRACT

A CPU acquires a distance image or a visible light image obtained by imaging a marker for measuring an SID as an object to be imaged using a TOF camera or a visible light camera. In addition, the CPU derives a marker distance between the TOF camera or the visible light camera and the marker from an image of a marker region corresponding to the marker in the acquired distance image or visible light image. Further, the CPU derives the SID on the basis of the derived marker distance and information indicating a positional relationship between an acquisition unit and the marker.

12 Claims, 7 Drawing Sheets

(51) Int. Cl.
  *G06T 7/521*    (2017.01)
  *G06T 7/60*     (2017.01)
  *G06T 7/70*     (2017.01)

(52) U.S. Cl.
  CPC .............. *G06T 2207/10028* (2013.01); *G06T 2207/10116* (2013.01); *G06T 2207/30204* (2013.01); *G06T 2207/30244* (2013.01)

(58) Field of Classification Search
  CPC . G06T 2207/30204; G06T 2207/30244; G01S 17/894
  See application file for complete search history.

(56) References Cited

U.S. PATENT DOCUMENTS

| | | | | |
|---|---|---|---|---|
| 2001/0053204 | A1* | 12/2001 | Navab | A61B 6/547 378/207 |
| 2014/0119500 | A1* | 5/2014 | Akahori | A61B 6/584 378/17 |
| 2015/0185340 | A1 | 7/2015 | Ye et al. | |
| 2015/0252938 | A1 | 9/2015 | Suzuki | |
| 2015/0356747 | A1* | 12/2015 | Dielacher | G06T 7/70 348/142 |
| 2016/0140720 | A1* | 5/2016 | Naito | A61B 6/5211 382/132 |
| 2016/0331334 | A1 | 11/2016 | Imamura et al. | |
| 2016/0374637 | A1* | 12/2016 | Lee | A61B 6/54 378/54 |
| 2016/0374642 | A1* | 12/2016 | Yamashita | A61B 6/589 378/204 |
| 2017/0172536 | A1* | 6/2017 | Song | A61B 6/583 |
| 2019/0046135 | A1* | 2/2019 | Hattori | G16H 50/30 |
| 2019/0110768 | A1* | 4/2019 | Lee | A61B 6/54 |
| 2021/0161501 | A1 | 6/2021 | Sendai | |

FOREIGN PATENT DOCUMENTS

| | | | | |
|---|---|---|---|---|
| JP | 2016-034300 | A | | 3/2016 |
| JP | 6142093 | B2 * | 6/2017 | .......... B65G 49/061 |
| JP | 2018-196791 | A | | 12/2018 |
| JP | 2019-033829 | A | | 3/2019 |
| JP | 2019103754 | A * | 6/2019 | |
| JP | 2020018702 | A * | 2/2020 | .......... A61B 6/5211 |
| WO | WO-2004052205 | A1 * | 6/2004 | .......... A61B 6/4441 |
| WO | WO-2005015125 | A1 * | 2/2005 | ............. A61B 6/027 |
| WO | WO-2013005833 | A1 * | 1/2013 | ............. A61B 6/025 |
| WO | 2015/079570 | A1 | | 6/2015 |
| WO | 2020/036225 | A1 | | 2/2020 |

OTHER PUBLICATIONS

Simultaneous 3D-2D image registration and C-arm calibration: Application to endovascular image-guided interventions, Uroš Mitrović et al., 2015, pp. 6433-6447 (Year: 2015).*
Assessment of Measurement Deviations: Length-extended X-ray Imaging for Orthopedic Applications, Christoph Luckner et al., SPIE, 2019, pp. 1094839-1 to 1094839-8 (Year: 2019).*
Geometrical Calibration of X-Ray Imaging With RGB Cameras for 3D Reconstruction, Francisco Albiol et al., IEEE, 2016, pp. 1952-1961 (Year: 2016).*
International Search Report issued in International Application No. PCT/JP2021/011504 on May 25, 2021.
Written Opinion of the ISA issued in International Application No. PCT/JP2021/011504 on May 25, 2021.
English language translation of the following: Office action dated Sep. 5, 2023 from the JPO in a Japanese patent application No. 2022-511928 corresponding to the instant patent application.

* cited by examiner

INFORMATION PROCESSING DEVICE, INFORMATION PROCESSING METHOD, AND INFORMATION PROCESSING PROGRAM

CROSS-REFERENCE TO RELATED APPLICATIONS

This application is a continuation application of International Application No. PCT/JP2021/011504, filed on Mar. 19, 2021, the disclosure of which is incorporated herein by reference in its entirety. Further, this application claims priority from Japanese Patent Application No. 2020-064479 filed on Mar. 31, 2020, the disclosure of which is incorporated herein by reference in its entirety.

BACKGROUND

1. Technical Field

The present disclosure relates to an information processing device, an information processing method, and an information processing program.

2. Description of the Related Art

In general, in a case in which a radiography apparatus captures radiographic images using a radiation detector, a distance between a radiation source and the radiation detector is detected. For example, according to a technique disclosed in JP2019-33829A, it is possible to measure a distance between a radiation source and a radiation detector on the basis of a camera image obtained by imaging a marker that is provided on a housing of an electronic cassette.

SUMMARY

In the technique disclosed in JP2019-33829A, the marker is provided on the housing of the electronic cassette. Therefore, for example, in a case in which the marker is hidden by a subject which is an object to be imaged, it may be difficult to appropriately measure the distance between the radiation source and the radiation detector.

The present disclosure has been made in view of the above circumstances, and an object of the present disclosure is to provide an information processing device, an information processing method, and an information processing program that can appropriately measure a distance between a radiation source and a radiation detector.

According to a first aspect of the present disclosure, there is provided an information processing device comprising at least one processor and a memory that stores commands executable by the processor. The processor acquires a captured image obtained by imaging a marker for measuring a distance between a radiation source and a radiation detector as an object to be imaged using an imaging device, derives a marker distance between the imaging device and the marker from an image of a marker region corresponding to the marker in the acquired captured image, and derives the distance between the radiation source and the radiation detector on the basis of the derived marker distance and information indicating a positional relationship between the radiation detector and the marker.

According to a second aspect of the present disclosure, in the information processing device according to the first aspect, the processor may derive the distance between the radiation source and the radiation detector further on the basis of information indicating a positional relationship between the imaging device and the radiation source.

According to a third aspect of the present disclosure, in the information processing device according to the first aspect or the second aspect, the object to be imaged may include a subject that is positioned between the radiation source and the radiation detector, and the processor may derive a subject distance between the imaging device and the subject from an image of a subject region corresponding to the subject in the acquired captured image and derive a body thickness of the subject on the basis of the derived subject distance and the distance between the radiation source and the radiation detector.

According to a fourth aspect of the present disclosure, in the information processing device according to the first aspect or the second aspect, the object to be imaged may include a subject that is positioned between the radiation source and the radiation detector, and the processor may derive a subject distance between the imaging device and the subject from an image of a subject region corresponding to the subject in the acquired captured image and derive a body thickness of the subject on the basis of the derived subject distance, the distance between the radiation source and the radiation detector, and a distance between the radiation detector and the subject.

According to a fifth aspect of the present disclosure, in the information processing device according to any one of the first to fourth aspects, the imaging device may be a distance image capture device that captures a distance image indicating a distance to the object to be imaged as the captured image, and the processor may derive a distance indicated by the image of the marker region corresponding to the marker in the distance image as the marker distance.

According to a sixth aspect of the present disclosure, in the information processing device according to the fifth aspect, the processor may specify the marker region in the distance image on the basis of a shape of the marker.

According to a seventh aspect of the present disclosure, in the information processing device according to the fifth aspect, the processor may acquire a visible light image obtained by imaging the marker as the object to be imaged using a visible light image capture device that captures the visible light image of the object to be imaged and set, as the marker region, a region of an image, which corresponds to a position of the marker specified by the image of the marker in the visible light image, in the distance image.

According to an eighth aspect of the present disclosure, in the information processing device according to any one of the fifth to seventh aspects, the distance image capture device may capture the distance image using a time-of-flight (TOF) method.

According to a ninth aspect of the present disclosure, in the information processing device according to any one of the first to fourth aspects, the imaging device may be a visible light image capture device that captures a visible light image of the object to be imaged as the captured image, and the processor may derive the marker distance on the basis of a size of the marker region in the visible light image and a reference size of the marker region associated with a reference value of the marker distance.

According to a tenth aspect of the present disclosure, in the information processing device according to any one of the first to ninth aspects, the processor may store the derived distance between the radiation source and the radiation detector in a storage unit and acquire the distance between the radiation source and the radiation detector from the storage unit to derive the distance between the radiation source and the radiation detector, without deriving the marker distance, in a case in which a position of the marker region specified from the captured image acquired currently is the same as a position of the marker region specified from the captured image acquired previously.

According to an eleventh aspect of the present disclosure, in the information processing device according to any one of the first to ninth aspects, the processor may store the derived distance between the radiation source and the radiation detector in a storage unit and output information indicating a warning for a period until the marker distance is derived from the captured image acquired currently in a case in which a position of the marker region specified from the captured image acquired currently is different from a position of the marker region specified from the captured image acquired previously.

Further, according to a twelfth aspect of the present disclosure, there is provided an information processing method executed by a computer. The information processing method comprises: acquiring a captured image obtained by imaging a marker for measuring a distance between a radiation source and a radiation detector as an object to be imaged using an imaging device; deriving a marker distance between the imaging device and the marker from an image of a marker region corresponding to the marker in the acquired captured image; and deriving the distance between the radiation source and the radiation detector on the basis of the derived marker distance and information indicating a positional relationship between the radiation detector and the marker.

In addition, according to a thirteenth aspect of the present disclosure, there is provided an information processing program that causes a computer to execute a process comprising: acquiring a captured image obtained by imaging a marker for measuring a distance between a radiation source and a radiation detector as an object to be imaged using an imaging device; deriving a marker distance between the imaging device and the marker from an image of a marker region corresponding to the marker in the acquired captured image; and deriving the distance between the radiation source and the radiation detector on the basis of the derived marker distance and information indicating a positional relationship between the radiation detector and the marker.

According to the present disclosure, it is possible to appropriately measure the distance between the radiation source and the radiation detector.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the disclosure will be described in detail with reference to the drawings. In addition, each of the embodiments does not limit the disclosure.

First Embodiment

Figure 1:
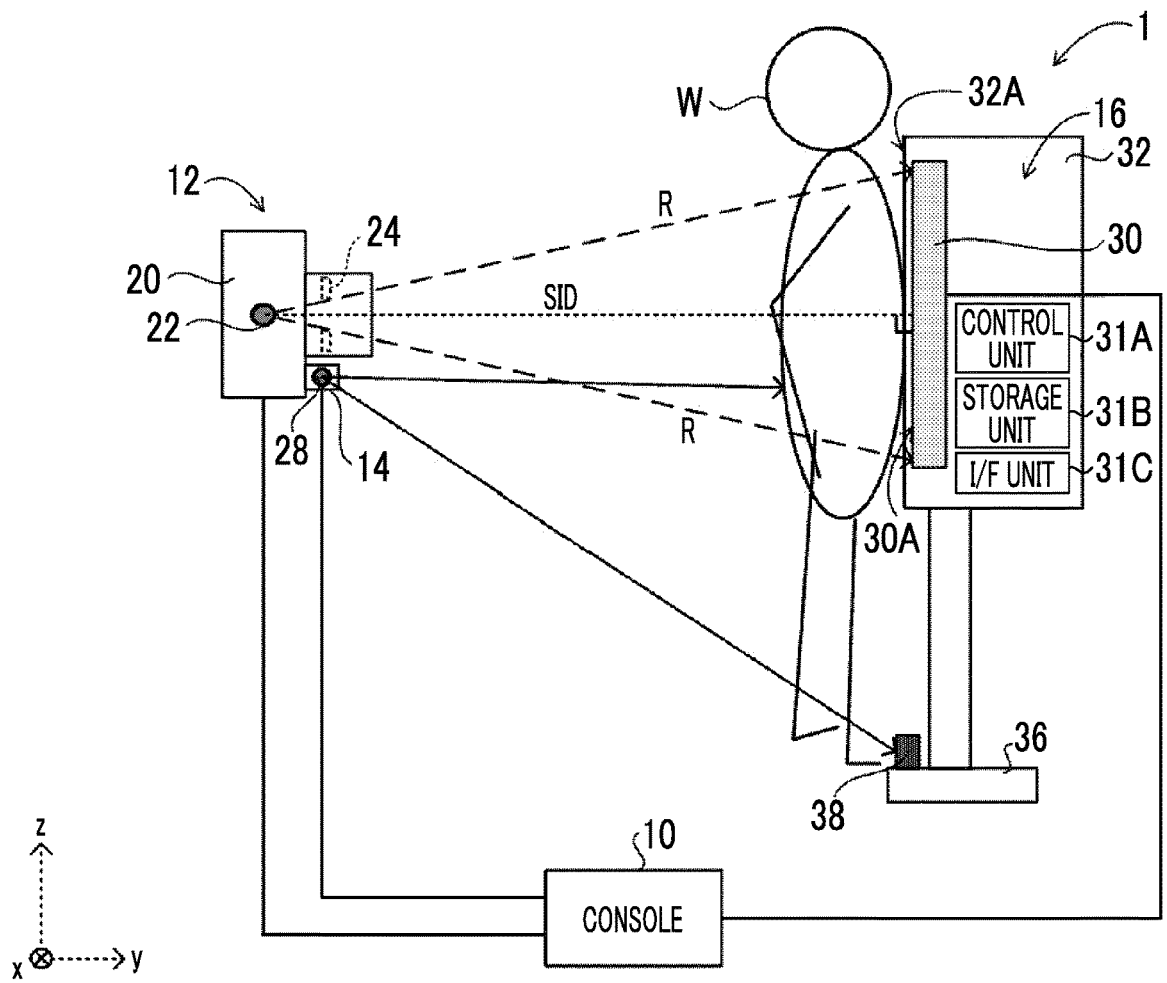
FIG. 1 is a diagram schematically illustrating an example of an overall configuration of a radiography system according to a first embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a console 10, a radiation emitting device 12, a time-of-flight (TOF) camera 14, and a radiography apparatus 16. The console 10 according to this embodiment is an example of an information processing device according to the present disclosure. In addition, FIG. 1 illustrates an aspect in which a radiographic image is captured in a state in which a subject W is standing up (standing state). However, the state of the subject W is not limited. For example, the subject W may be in a state (sitting state) in which it is sitting on a chair (including a wheelchair) and the like.

The radiation emitting device 12 according to this embodiment comprises a radiation source 20 that irradiates the subject W, which is an example of an object to be imaged, with radiation R, such as X-rays, and a collimator 24 that limits an irradiation field of the radiation R emitted from the radiation source 20. In addition, the radiation emitting device 12 comprises a radiation source control unit (not illustrated) that controls the radiation source 20 and the collimator 24.

A method by which a user, such as a doctor or a technician, instructs the radiation emitting device 12 to emit the radiation R is not limited. For example, in a case in which the radiation emitting device 12 is provided with an irradiation button or the like, the user, such as a radiology technician, may input an instruction to emit the radiation R with the irradiation button such that the radiation R is emitted from the radiation emitting device 12. Further, for example, the user, such as the radiology technician, may operate the console 10 to input the instruction to emit the radiation R such that the radiation R is emitted from the radiation emitting device 12.

In a case in which the radiation emitting device 12 receives the instruction to emit the radiation R, it emits the radiation R from a focus 22 of a radiation tube of the radiation source 20 according to irradiation conditions, such as the set tube voltage, tube current, and irradiation period, under the control of the radiation source control unit. For example, in this embodiment, the irradiation field has a rectangular shape. Therefore, a rectangular-pyramid-shaped region that has the focus 22 as the apex and the irradiation field as the base is irradiated with the radiation R emitted from the focus 22.

Further, as illustrated in FIG. 1, the TOF camera 14 is provided in the vicinity of an exit port through which the radiation R is emitted from the radiation emitting device 12. The TOF camera 14 is a camera that captures a distance image indicating a distance to the object to be imaged using the TOF method with an imaging element 28. The TOF camera 14 according to this embodiment is an example of an imaging device and a distance image capture device according to the present disclosure. Specifically, the TOF camera 14 emits light, such as infrared rays, to the object to be imaged and measures the distance between the TOF camera 14 and the object to be imaged on the basis of the time until a reflected light is received or a phase change between the emitted light and the received light. In the distance image captured by the TOF camera 14, each pixel has distance information indicating the distance between the TOF camera 14 and the object to be imaged. In addition, in the TOF camera 14 according to this embodiment, the distance between the imaging element 28 and the object to be imaged is applied as the distance between the TOF camera 14 and the object to be imaged. Further, the distance image is an image from which the distance to the object to be imaged can be derived.

The radiography apparatus 16 comprises a radiation detector 30, a control unit 31A, a storage unit 31B, and an interface (I/F) unit 31C.

The radiation detector 30 has a function of generating a radiographic image. As illustrated in FIG. 1, the radiation detector 30 is disposed in an imaging table 32. In the radiography apparatus 16 according to this embodiment, in a case in which imaging is performed, the subject W is positioned on an imaging surface 32A of the imaging table 32 by the user.

The radiation detector 30 detects the radiation R transmitted through the subject W and the imaging table 32, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

The control unit 31A controls the overall operation of the radiography apparatus 16 under the control of the console 10. The control unit 31A comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by the radiation detector 30 and various other kinds of information are stored in the storage unit 31B. Specific examples of the storage unit 31B include a hard disk drive (HDD) and a solid state drive (SSD). The I/F unit 31C transmits and receives various kinds of information to and from the console 10 using wireless communication or wired communication. The image data of the radiographic image captured by the radiation detector 30 is transmitted to the console 10 through the I/F unit 31C by wireless communication or wired communication.

In addition, a base 36 of the imaging table 32 according to this embodiment is provided with a marker 38 for measuring the distance between the radiation source 20 and the radiation detector 30 (SID: source to image receptor distance; hereinafter, referred to as an "SID"). The marker 38 according to this embodiment is an example of a marker according to the present disclosure. The marker 38 is provided at a position that is not hidden by the positioned subject W. Specifically, in the capture of the distance image by the TOF camera 14, the marker 38 is provided at a position that is not hidden by the subject W. In this embodiment, the size and shape of the marker 38 are predetermined. Further, in this embodiment, the SID means the length of a perpendicular line drawn from the focus 22 of the radiation source 20 to the detection surface 30A of the radiation detector 30 as illustrated in FIG. 1.

Meanwhile, the console 10 according to this embodiment has a function of controlling the radiation emitting device 12, the TOF camera 14, and the radiography apparatus 16 using, for example, an imaging order and various kinds of information acquired from a radiology information system (RIS) (not illustrated) or the like through a wireless communication local area network (LAN) or the like.

Figure 2:
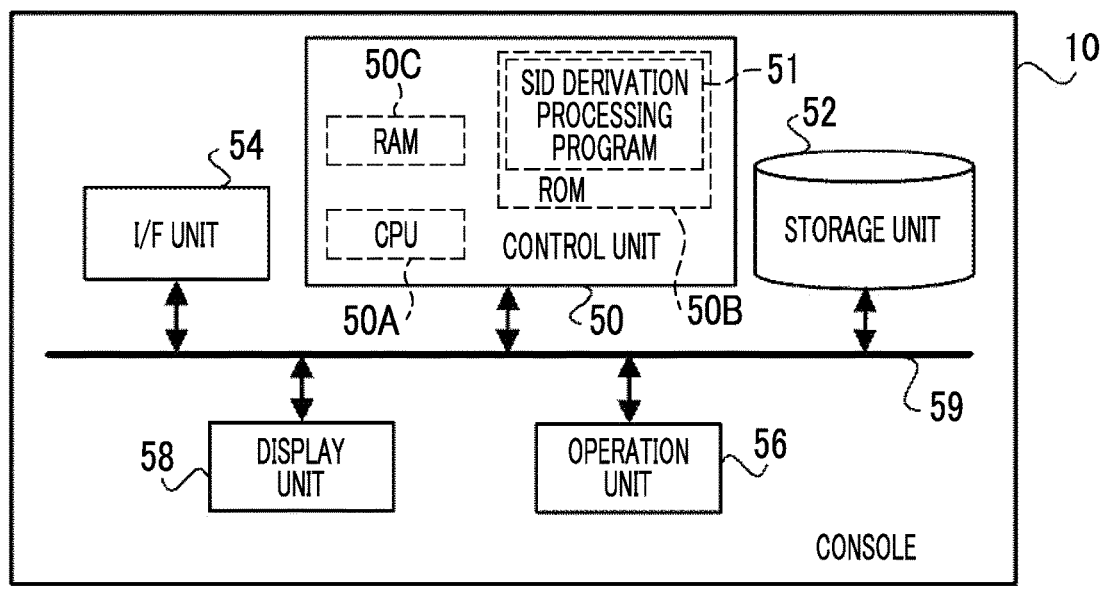
FIG. 2 is a block diagram illustrating an example of a configuration of a console according to the first embodiment.

For example, the console 10 according to this embodiment is a server computer. As illustrated in FIG. 2, the console 10 comprises a control unit 50, a storage unit 52, an I/F unit 54, an operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 10. The control unit 50 comprises a CPU 50A, a ROM 50B, and a RAM 50C. For example, various programs including an SID derivation processing program 51 executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure. Further, the SID derivation processing program 51 according to this embodiment is an example of an information processing program according to the present disclosure.

For example, the image data of the radiographic image captured by the radiography apparatus 16 and various other kinds of information (which will be described in detail below) are stored in the storage unit 52. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the radiography apparatus 16 and the RIS (not illustrated) using wireless communication or wired communication. In the radiography system 1 according to this embodiment, the console 10 receives the image data of the radiographic image captured by the radiography apparatus 16 from the radiography apparatus 16 through the I/F unit 54, using wireless communication or wired communication.

Figure 3:
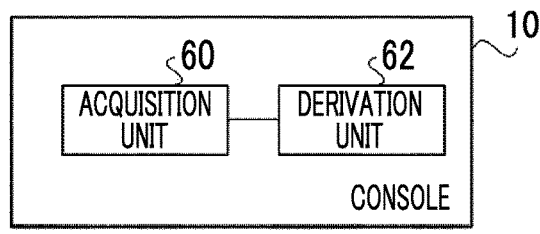
FIG. 3 is a functional block diagram illustrating an example of a functional configuration of the console according to the first embodiment.

In addition, FIG. 3 is a functional block diagram illustrating an example of the functional configuration of the console 10 according to this embodiment. As illustrated in FIG. 3, the console 10 comprises an acquisition unit 60 and a derivation unit 62. For example, in the console 10 according to this embodiment, the CPU 50A of the control unit 50 executes the SID derivation processing program 51 stored in the ROM 50B to function as the acquisition unit 60 and the derivation unit 62.

The acquisition unit 60 has a function of acquiring the distance image captured by the TOF camera 14. For example, the acquisition unit 60 according to this embodiment acquires image data indicating the distance image captured by the TOF camera 14 from the TOF camera 14 through the I/F unit 31C and the I/F unit 54. The image data indicating the distance image acquired by the acquisition unit 60 is output to the derivation unit 62.

The derivation unit 62 has a function of deriving the SID. Specifically, the derivation unit 62 derives the distance between the TOF camera 14 and the marker 38 (hereinafter, referred to as a marker distance) from an image of a region (hereinafter, referred to as a marker region) corresponding to the marker 38 in the distance image. The marker region according to this embodiment is an example of a marker region according to the present disclosure, and the marker distance according to this embodiment is an example of a marker distance according to the present disclosure. Further, the derivation unit 62 derives the SID on the basis of the marker distance and information indicating the positional relationship between the radiation detector 30 and the marker 38.

Figure 4A:
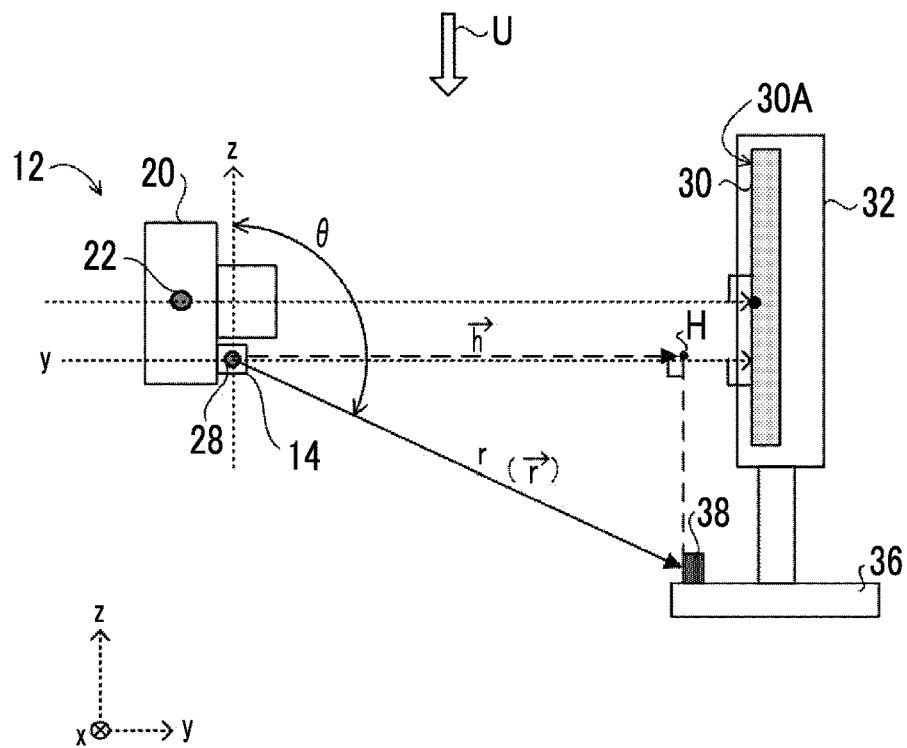
FIG. 4A is a schematic diagram illustrating an example of a positional relationship among a focus of a radiation emitting device, an imaging element of a TOF camera, a radiation detector, and a marker as viewed from an X-axis direction.
Figure 4B:
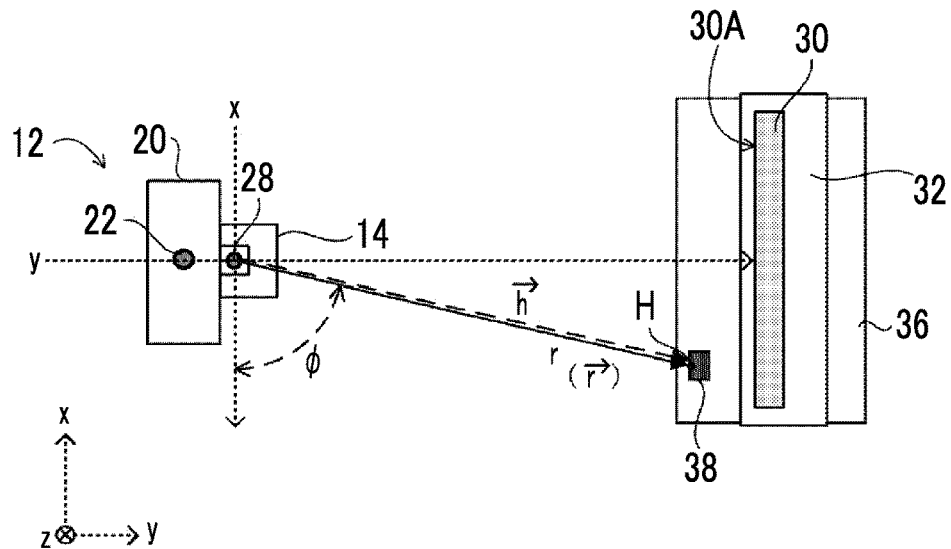
FIG. 4B is a schematic diagram illustrating an example of a positional relationship among the focus of the radiation emitting device, the imaging element of the TOF camera, the radiation detector, and the marker as viewed from a Z-axis direction.
Figure 5:
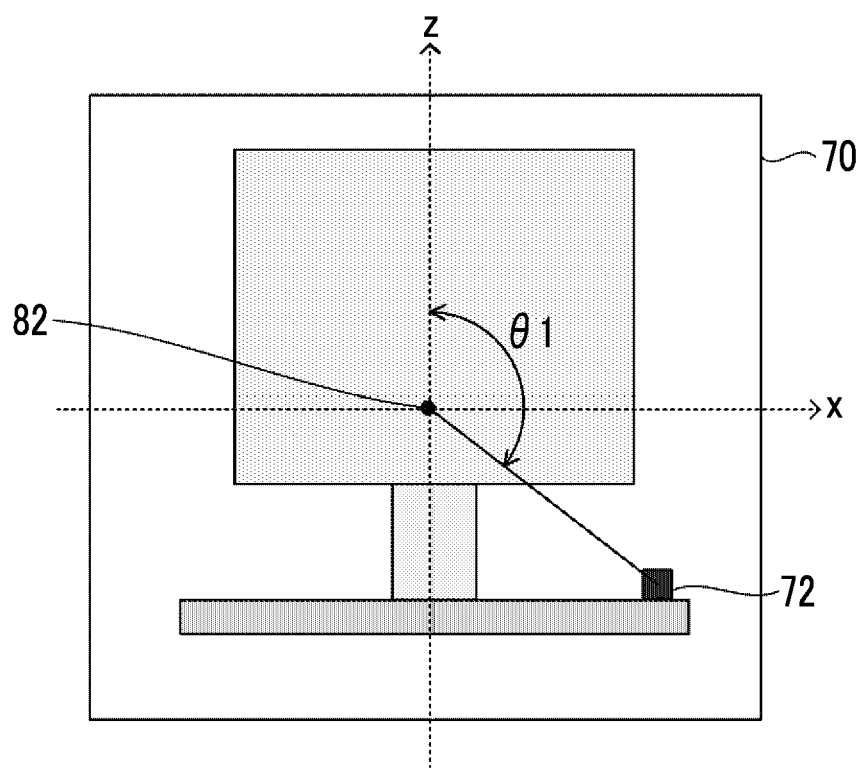
FIG. 5 is a diagram illustrating an example of a distance image captured by the TOF camera.

Here, a method by which the derivation unit 62 according to this embodiment derives the SID will be described in detail with reference to FIGS. 4A to 5. FIG. 4A is a schematic diagram illustrating an example of the positional relationship among the focus 22 of the radiation emitting device 12, the imaging element 28 of the TOF camera 14, the radiation detector 30, and the marker 38 as viewed from the X-axis direction. Further, FIG. 4B is a schematic diagram illustrating an example of the positional relationship among the focus 22 of the radiation emitting device 12, the imaging element 28 of the TOF camera 14, the radiation detector 30, and the marker 38 as viewed from the Z-axis direction (from the side of an arrow U in FIG. 4A). FIG. 5 illustrates an example of a distance image 70 captured by the TOF camera 14. In addition, in FIG. 4A, FIG. 4B, and FIG. 5, the illustration of the subject W is omitted for convenience of illustration omission.

A vector from the focus 22 to the radiation detector 30 which has the same length as the SID is represented by the addition of a vector from the focus 22 to the imaging element 28, a vector $\vec{r}$ from the imaging element 28 to the marker 38, and a vector from the marker 38 to the radiation detector 30. Therefore, the length of the vector obtained by adding the vector from the focus 22 to the imaging element 28, the vector $\vec{r}$ from the imaging element 28 to the marker 38, and the vector from the marker 38 to the radiation detector 30 is the SID.

In this embodiment, the SID is derived using a polar coordinate system in which the position of the imaging element 28 of the TOF camera 14 is set as the origin having the coordinates (0, 0, 0) and the position of the marker 38, the position of the radiation detector 30, and the position of the focus 22 of the radiation source 20 are represented by three parameters of (r, θ, φ).

It is assumed that the positional relationship between the focus 22 and the imaging element 28 is $(x_1, y_1, z_1)$. For example, in the radiography system 1 according to this embodiment, the positional relationship $(x_1, y_1, z_1)$ does not change and is set to a fixed value. Further, in this embodiment, the positional relationship $(x_1, y_1, z_1)$ is stored in advance as information indicating the positional relationship between the focus 22 and the imaging element 28, for example, in a storage unit (not illustrated) of the radiation emitting device 12. The positional relationship $(x_1, y_1, z_1)$ according to this embodiment is an example of information indicating a positional relationship between an imaging device and a radiation source according to the present disclosure.

Meanwhile, it is assumed that the positional relationship between the imaging element 28 and the marker 38 is $(x_2, y_2, z_2)$. For example, in the radiography system 1 according to this embodiment, the positional relationship $(x_2, y_2, z_2)$ changes and is not set to a fixed value.

Further, it is assumed that the positional relationship between the marker 38 and the radiation detector 30 is $(x_3, y_3, z_3)$. For example, in the radiography system 1 according to this embodiment, the positional relationship $(x_3, y_3, z_3)$ does not change and is set to a fixed value. Further, in this embodiment, the positional relationship $(x_3, y_3, z_3)$ is stored in advance as information indicating the positional relationship between the marker 38 and the radiation detector 30 in, for example, the storage unit 31B (not illustrated in FIGS. 4A and 4B) of the radiography apparatus 16. The positional relationship $(x_3, y_3, z_3)$ according to this embodiment is an example of information indicating the positional relationship between the radiation detector and the marker according to the present disclosure.

Furthermore, it is assumed that is a vector from the imaging element 28 (0, 0, 0) to the marker 38 is $\vec{r}$ and the distance between the imaging element 28 and the marker 38 is r. Moreover, it is assumed that an intersection point between the foot of a perpendicular line drawn from the marker 38 to an X-Y plane of Z=0 through the imaging element 28 (0, 0, 0) and the X-Y plane is H. In addition, it is assumed that a vector from the imaging element 28 to the intersection point H is $\vec{h}$. In FIG. 4B, the vector $\vec{h}$ appears to overlap the vector $\vec{r}$.

The angle θ that defines the polar coordinate system is an angle formed between the vector $\vec{r}$ connecting the imaging element 28 (0, 0, 0) and the marker 38 and the z-axis. In addition, the angle φ that defines the polar coordinate system is an angle formed between the vector $\vec{h}$ and the x-axis. The angle θ and the angle φ can be derived from the position of a marker image 72 indicating the marker 38 in the distance image 70. For example, as illustrated in FIG. 5, the angle θ is reflected in an angle θ1 formed between a straight line connecting a center 82 of the distance image 70 corresponding to the position of the imaging element 28 and the marker image 72 and the z-axis passing through the center 82. Specifically, the angles can be derived from the number of pixels of the marker image 72 in each of the vertical direction (z direction) and the horizontal direction (x direction) in the distance image 70 and the angle of view of the TOF camera 14. In addition, the marker image 72 according to this embodiment is an example of an image of the marker region corresponding to the marker according to the present disclosure.

The position (r, θ, φ) of the marker 38 in the polar coordinate system can be converted into a rectangular coordinate system ($x_2$, $y_2$, $z_2$) by the following Expression (1) to (3).

$$x_2 = r \times \sin\theta \times \cos\varphi \quad (1)$$

$$y_2 = r \times \sin\theta \times \sin\varphi \quad (2)$$

$$z_2 = r \times \cos\theta \quad (3)$$

Therefore, the SID can be derived from the positional relationship ($x_1$, $y_1$, $z_1$) between the focus 22 and the imaging element 28 and the positional relationship ($x_2$, $y_2$, $z_2$) between the imaging element 28 and the marker 38, and the positional relationship ($x_3$, $y_3$, $z_3$) between the marker 38 and the radiation detector 30 by the following Expression (4).

$$SID = \sqrt{x^2 + y^2 + z^2} \quad (4)$$

(where (x, y, z) = ($x_1+x_2+x_3$, $y_1+y_2+y_3$, $z_1+z_2+z_3$))

In addition, as described above, since the SID is the distance of the perpendicular line from the focus 22 to the detection surface 30A of the radiation detector 30, it may be derived by the following Expression (5).

$$SID = y_1 + y_2 + y_3 \quad (5)$$

Further, the derivation unit 62 according to this embodiment has a function of deriving a body thickness of the positioned subject W. For example, in this embodiment, a value obtained by subtracting the distance between the imaging element 28 and the subject W and the distance between the detection surface 30A of the radiation detector 30 and the imaging surface 32A of the imaging table 32 from the derived SID is derived as the body thickness of the subject W. The distance between the detection surface 30A of the radiation detector 30 and the imaging surface 32A of the imaging table 32 is a value obtained from, for example, the design values of the radiation detector 30 and the imaging table 32 and is stored in advance, for example, in the storage unit 31B of the radiography apparatus 16 in this embodiment. In addition, in a case in which a predetermined condition is satisfied, for example, in a case in which the distance between the detection surface 30A of the radiation detector 30 and the imaging surface 32A of the imaging table 32 is sufficiently short, the distance may be ignored in the derivation of the body thickness.

Next, the operation of the console 10 according to this embodiment will be described with reference to the drawings.

Figure 6:
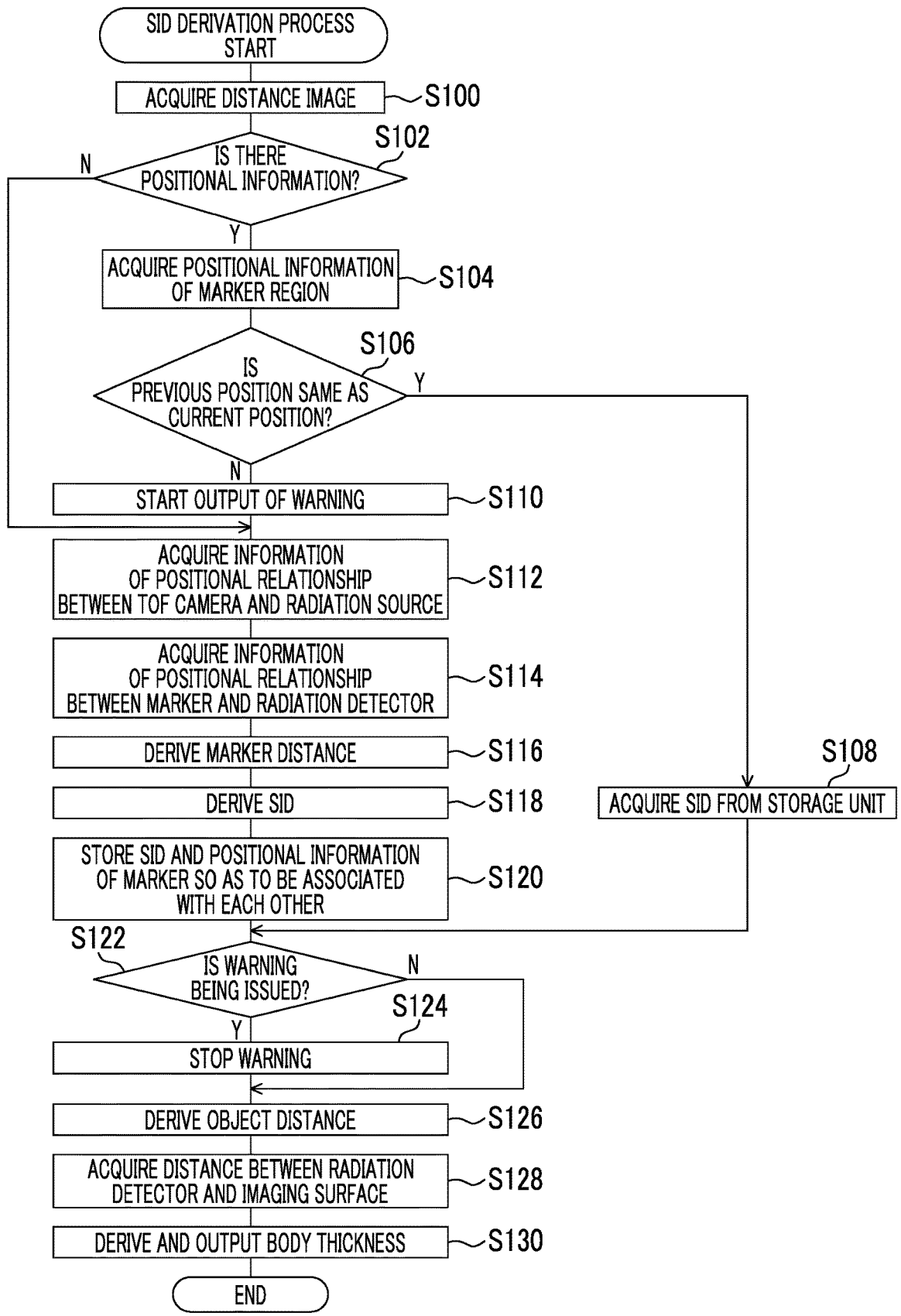
FIG. 6 is a flowchart illustrating an example of a flow of an SID derivation process of the console according to the first embodiment.

In the console 10 according to this embodiment, the CPU 50A of the control unit 50 executes the SID derivation processing program 51 stored in the ROM 50B to perform an SID derivation process whose example is illustrated in FIG. 6. FIG. 6 is a flowchart illustrating an example of the flow of the SID derivation process performed in the console 10 according to this embodiment. In addition, the timing when the CPU 50A performs the SID derivation process is not limited, and the CPU 50A may perform the SID derivation process at any timing. For example, the SID derivation process may be performed at the timing when an instruction input from the user by the operation of the operation unit 56 after the positioning of the subject W ends is received or the timing when an instruction to emit the radiation R from the user is received.

In Step S100 of FIG. 6, the acquisition unit 60 acquires the distance image from the TOF camera 14. Specifically, the acquisition unit 60 instructs the TOF camera 14 to capture a distance image and acquires the distance image captured by the TOF camera 14 on the basis of the instruction through the I/F unit 54. The distance image acquired by the acquisition unit 60 is output to the derivation unit 62.

Then, in Step S102, the derivation unit 62 determines whether or not positional information indicating the position of the marker region corresponding to the marker 38 in the distance image 70 is stored in the storage unit 52. Specifically, the positional information of the marker region is information indicating the position of the marker image 72 in the distance image 70 and the size of the marker image 72. For example, in this embodiment, the distance image 70 including the marker image 72 is adopted as the positional information of the marker region. In this embodiment, in a case in which the SID is derived, the positional information of the marker region is stored in the storage unit 52 to be associated with the derived SID, which will be described in detail below. Therefore, the derivation unit 62 determines whether or not the positional information of the marker region is stored in the storage unit 52 in association with the SID used in the previous process. In a case in which the positional information of the marker region is not stored in the storage unit 52, for example, in a case in which the radiography system 1 is operated for the first time to capture a radiographic image, the determination result in Step S102 is "No", and the process proceeds to Step S112. On the other hand, in a case in which the positional information of the marker region is stored in the storage unit 52, the determination result in Step S102 is "Yes", and the process proceeds to Step S104.

In Step S104, the derivation unit 62 acquires the positional information of the marker region from the storage unit 52. Then, in Step S106, the derivation unit 62 determines whether or not the position of the marker region in the previous distance image 70 is the same as the position of the marker region in the current distance image 70. Specifically, it is determined whether or not the position and size (the number of pixels) of the marker image 72 in the previous distance image 70 used to derive the SID, which is the positional information of the marker region acquired in Step S104, are the same as the position and size of the marker image 72 in the current distance image 70 which has been captured by the TOF camera 14 and acquired in Step S100.

In addition, in this embodiment, a method of extracting an image corresponding to the shape of the marker 38 in the distance image 70 is adopted as the method by which the derivation unit 62 specifies the marker image 72 from the distance image 70. In a case in which the shape of the marker 38 is a characteristic shape such as a triangular shape, an image corresponding to the characteristics may be extracted from the distance image 70. Further, even in a case in which the shape of the marker 38 is a general shape such as a rectangular shape, a condition for defining the shape may be defined. For example, in a case in which the marker 38 has a rectangular shape, a width-to-height ratio may be defined. An image in which the width-to-height ratio is a predetermined ratio may be extracted from the distance image 70.

In a case in which the position of the marker region in the previous distance image 70 is the same as the position of the marker region in the current distance image 70, the determination result in Step S106 is "Yes", and the process proceeds to Step S108. In a case in which the position of the marker region in the previous distance image 70 is the same as the position of the marker region in the current distance image 70, the SID derived from the previous distance image 70 is equal to the SID derived from the current distance image 70. Therefore, the previously derived SID can be applied to the current capture of the radiographic image without newly deriving the SID. Therefore, in Step S108, the derivation unit 62 acquires the SID stored in the storage unit 52 in association with the positional information of the marker region from the storage unit 52 and then proceeds to Step S122.

On the other hand, in a case in which the position of the marker region in the previous distance image 70 is different from the position of the marker region in the current distance image 70, the determination result in Step S106 is "No", and the process proceeds to Step S110. In Step S110, the derivation unit 62 starts outputting information indicating a predetermined warning. In addition, the specific content of the warning, the output destination of the warning, and a warning method are not particularly limited. For example, as the content of the warning, the fact that preparations are being made may be displayed on the display unit 58 in at least one of a visible display manner or an audible display manner.

Then, in Step S112, the derivation unit 62 acquires information indicating the positional relationship between the TOF camera 14 and the radiation source 20. Specifically, in this embodiment, as described above, the positional relationship ($x_1$, $y_1$, $z_1$) between the focus 22 and the imaging element 28 is acquired.

Then, in Step S114, the acquisition unit 60 acquires information indicating the positional relationship between the marker 38 and the radiation detector 30. Specifically, in this embodiment, as described above, the positional relationship ($x_3$, $y_3$, $z_3$) between the marker 38 and the radiation detector 30 is acquired.

Then, in Step S116, the derivation unit 62 derives the marker distance from the TOF camera 14 (imaging element 28) to the marker 38. Specifically, the marker distance is derived on the basis of the pixel value of an image corresponding to the marker image 72 included in the distance image 70 acquired in Step S100. Then, in Step S118, the derivation unit 62 derives the SID using the above-described Expression (4) or (5) as described above.

Then, in Step S120, the derivation unit 62 stores the SID derived in the Step S118 and the positional information of the marker region in the storage unit 52 to be associated with each other. As described above, for example, the derivation unit 62 according to this embodiment stores the SID derived in Step S118 in the storage unit 52 to be associated with the distance image 70 acquired in Step S100.

In Step S122 following Step S108 or Step S120, the acquisition unit 60 determines whether or not a warning is being issued. In a case in which the information indicating the warning is output by the process in Step S110, the determination result in Step S122 is "Yes", and the process proceeds to Step S124. In Step S124, the derivation unit 62 stops outputting the information indicating the warning and then proceeds to Step S126. On the other hand, in a case in which the information indicating the warning is not output, the determination result in Step S122 is "No", and the process proceeds to Step S126.

In Step S126, the derivation unit 62 derives an subject distance from the TOF camera 14 to the subject W. Specifically, the derivation unit 62 derives the distance from the imaging element 28 to a body surface of the subject W facing the radiation emitting device 12 on the basis of the pixel value of an image corresponding to the subject W included in the distance image 70 acquired in Step S100. In addition, the subject distance derived here may be, for example, the distance between the position of the subject W facing the imaging element 28 and the imaging element 28 or the distance between the imaging element 28 and the position of the subject W having the largest thickness in the capture range of the radiographic image. The distance to which position of the subject W the subject distance is set as is not limited, and any subject distance may be used.

Then, in Step S128, the derivation unit 62 acquires the distance between the detection surface 30A of the radiation detector 30 and the imaging surface 32A of the imaging table 32 as described above. Then, in Step S130, the derivation unit 62 derives the body thickness of the subject W as described above. Specifically, the derivation unit 62 subtracts the subject distance derived in Step S126 and the distance between the detection surface 30A of the radiation detector 30 and the imaging surface 32A of the imaging table 32 acquired in Step S128 from the SID acquired in Step S108 or the SID derived in Step S118.

The body thickness of the subject W derived in this way is used, for example, for setting imaging conditions. Examples of the imaging conditions include the values of the tube voltage and the tube current of the radiation source 20 of the radiation emitting device 12 and the irradiation time of the radiation R which are imaging conditions determined by the body thickness and imaging part of the subject W. Therefore, the derivation unit 62 outputs information indicating the derived body thickness to a predetermined output destination in order to set the imaging conditions. In a case in which Step S130 ends in this way, this SID derivation process ends.

As described above, in this embodiment, the derivation unit 62 derives the marker distance between the TOF camera 14 and the marker 38 from the image of the marker region corresponding to the marker 38 in the distance image captured by the TOF camera 14. Further, the derivation unit 62 derives the SID on the basis of the derived marker distance and information indicating the positional relationship between the radiation detector 30 and the marker 38. Therefore, according to the console 10 of this embodiment, the SID can be measured by the marker 38 that is provided at a position away from the radiation detector 30 and the imaging table 32. Therefore, it is possible to appropriately measure the SID.

In addition, in this embodiment, the aspect in which the derivation unit 62 extracts an image corresponding to the shape of the marker 38 from the distance image 70 to specify the marker image 72 and the marker region. However, a method for specifying the marker image 72 and the marker region from the distance image 70 is not limited to this embodiment. For example, a visible light camera (see a visible light camera 15 in a second embodiment of FIG. 7) may be provided together with the TOF camera 14, and the marker image 72 and the marker region may be specified using a visible light image captured by the visible light camera. In this case, a position on the distance image 70 and a position on the visible light image captured by the visible light camera are aligned in advance on the basis of a position in the real space. Then, image recognition is applied to the visible light image captured by the visible light camera, an image indicating the marker 38 is detected from the visible light image, and an image and a region in the distance image 70 corresponding to the position of the marker image 72 and the marker region specified by the detected image are used as the marker image 72 and the marker region.

Second Embodiment

In the first embodiment, the aspect in which the SID is derived using the distance image captured by the TOF camera 14 has been described. In contrast, in this embodiment, an aspect in which the SID is derived using a visible light image captured by a visible light camera will be described. In addition, for a console 10, a radiation emitting device 12, and a radiation detector 30 according to this embodiment, the detailed description of the same configurations and operations as those in the first embodiment will be omitted.

Figure 7:
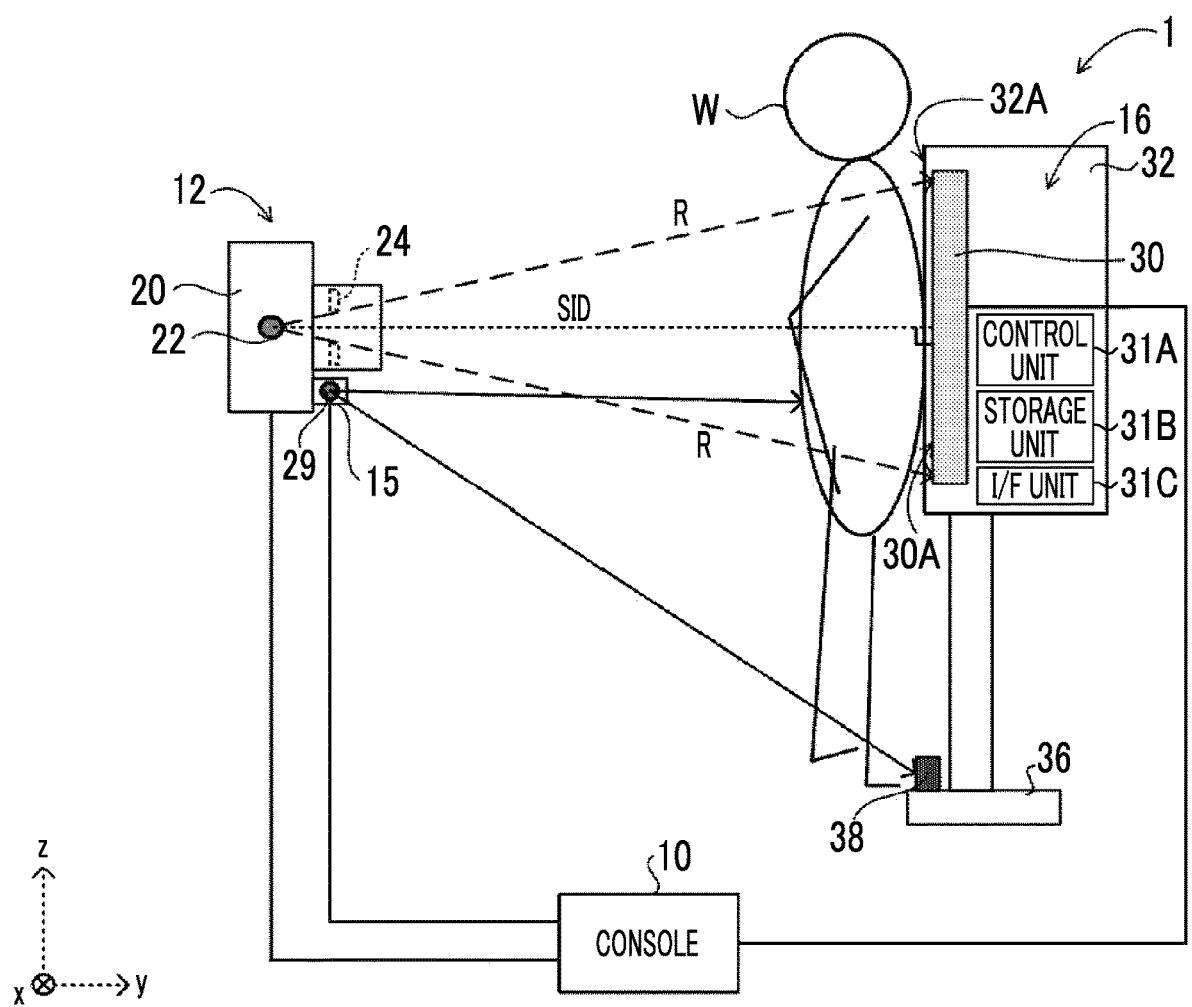
FIG. 7 is a diagram schematically illustrating an example of an overall configuration of a radiography system according to a second embodiment.

FIG. 7 is a diagram illustrating an example of the overall configuration of a radiography system 1 according to this embodiment. As illustrated in FIG. 7, the radiography system 1 according to this embodiment comprises a visible light camera 15 having an imaging element 29 instead of the TOF camera 14 according to the first embodiment. The visible light camera 15 is a so-called general camera and captures a visible light image. The visible light camera 15 according to this embodiment is an example of the imaging device and a visible light image capture device according to the present disclosure. Specifically, the visible light camera 15 receives visible light reflected by an object to be imaged using the imaging element 29 and captures a visible light image on the basis of the received visible light.

In addition, an acquisition unit 60 according to this embodiment has a function of acquiring the visible light image captured by the visible light camera 15. For example, the acquisition unit 60 according to this embodiment acquires image data indicating the visible light image captured by the visible light camera 15 from the visible light camera 15 through the I/F unit 54. The image data indicating the visible light image acquired by the acquisition unit 60 is output to a derivation unit 62.

Further, the derivation unit 62 according to this embodiment has a function of deriving the SID on the basis of the visible light image and derives the marker distance from the image of the marker region in the visible light image.

Specifically, the size of the marker region in the visible light image captured by the visible light camera 15 in a state in which the marker distance is set as a reference value, specifically, the position and size (the number of pixels) of the marker region in the visible light image are acquired as a reference size in advance. In other words, the reference size of the marker region associated with the reference value of the marker distance is acquired in advance and stored in, for example, the storage unit 31B of the radiography apparatus 16. The derivation unit 62 derives the marker distance on the basis of the size of the marker region in the visible light image acquired by the acquisition unit 60 and the reference size of the marker region associated with the reference value of the marker distance. For example, in a case in which the size of the marker region in the visible light image acquired by the acquisition unit 60 is 1.5 times the reference size of the marker region, the derivation unit 62 derives a value that is one third of the reference value of the marker distance as the current marker distance. The derivation unit 62 derives the SID using the derived marker distance in the same manner as that in the first embodiment.

Further, the operation of the console 10 according to this embodiment, specifically, an SID derivation process performed by the console 10 will be described.

Figure 8:
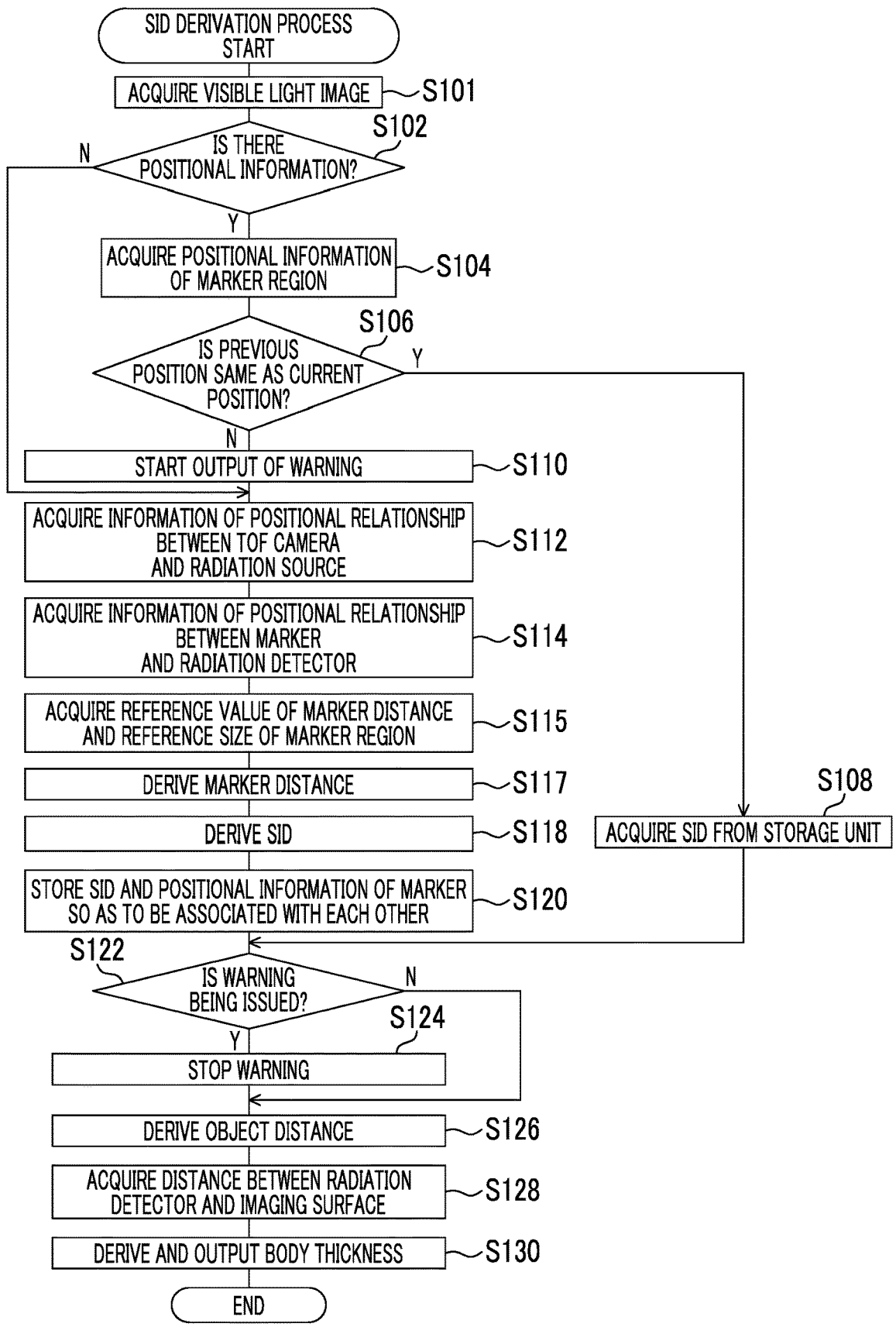
FIG. 8 is a flowchart illustrating an example of a flow of an SID derivation process of a console according to the second embodiment.

FIG. 8 is a flowchart illustrating an example of the flow of the SID derivation process performed in the console 10 according to this embodiment. As illustrated in FIG. 8, the SID derivation process according to this embodiment includes a process in Step S101 instead of Step S100 in the SID derivation process (see FIG. 6) according to the first embodiment.

In Step S101 of FIG. 8, the acquisition unit 60 acquires a visible light image from the visible light camera 15 as described above. Specifically, the acquisition unit 60 instructs the visible light camera 15 to capture a visible light image and acquires a visible light image captured by the visible light camera 15 on the basis of the instruction through the I/F unit 54. The visible light image acquired by the acquisition unit 60 is output to the derivation unit 62.

Further, the SID derivation process according to this embodiment includes processes in Steps S115 and S117 instead of Step S116 of the SID derivation process (see FIG. 6) according to the first embodiment.

In Step S115, the derivation unit 62 acquires the reference value of the marker distance and the reference size of the marker region as described above. Then, in Step S117, the derivation unit 62 derives the marker distance as described above. Specifically, the size of the marker region in the visible light image acquired in Step S101 is derived. Then, the derived size of the marker region is compared with the reference size of the marker region acquired in Step S115. Further, the marker distance is derived on the basis of the comparison result and the reference value of the marker distance.

As described above, in this embodiment, the SID can be derived using the visible light image captured by the visible light camera 15. Therefore, according to the console 10 of this embodiment, the SID can be measured by the marker 38 that is provided at a position away from the radiation detector 30 and the imaging table 32. Therefore, it is possible to appropriately measure the SID.

As described above, the console 10 according to each of the above-described embodiments comprises the CPU 50A as at least one processor and the ROM 50B storing commands that can be executed by the CPU 50A. The CPU 50A acquires the distance image or the visible light image obtained by imaging the marker 38 for measuring the SID as the object to be imaged with the TOF camera 14 or the visible light camera 15. In addition, the CPU 50A derives the marker distance between the TOF camera 14 or the visible light camera 15 and the marker 38 from the image of the marker region corresponding to the marker 38 in the acquired distance image or visible light image. Further, the CPU 50A derives the SID on the basis of the derived marker distance and information indicating the positional relationship between the acquisition unit 60 and the marker 38.

As described above, according to the console 10 of this embodiment, it is possible to measure the SID on the basis of the distance image or the visible light image obtained by imaging the marker 38 as the object to be imaged.

Therefore, according to the console 10 of this embodiment, the SID can be measured by the marker 38 that is provided at a position away from the radiation detector 30 and the imaging table 32. Therefore, it is possible to appropriately measure the SID. For example, even in a case in which the radiation detector 30 or the imaging table 32 is hidden by the subject, it is possible to measure the SID.

In addition, in each of the above-described embodiments, the aspect in which the console 10, the radiation emitting device 12, and the radiography apparatus 16 are stationary systems in the radiography system 1 has been described. However, the radiography system 1 is not limited to this embodiment. For example, a mobile cart, that is, a nursing cart may be used as the radiography system 1. Further, in each of the above-described embodiments, since the marker 38 is fixed to the base 36 of the imaging table 32, the disposition of the marker 38 with respect to the radiation detector 30 is fixed. Meanwhile, in the case of the nursing cart or the like, each of the radiation detector 30 and the marker 38 is handled individually. Therefore, the disposition of the marker 38 with respect to the radiation detector 30 may not be fixed. In this case, a jig having a predetermined length in which the marker 38 is disposed may be attached to an attachment position of a housing or the like that includes the radiation detector 30, and the SID may be derived using the distance image or the captured image as in each of the above-described embodiments.

Figure 9:
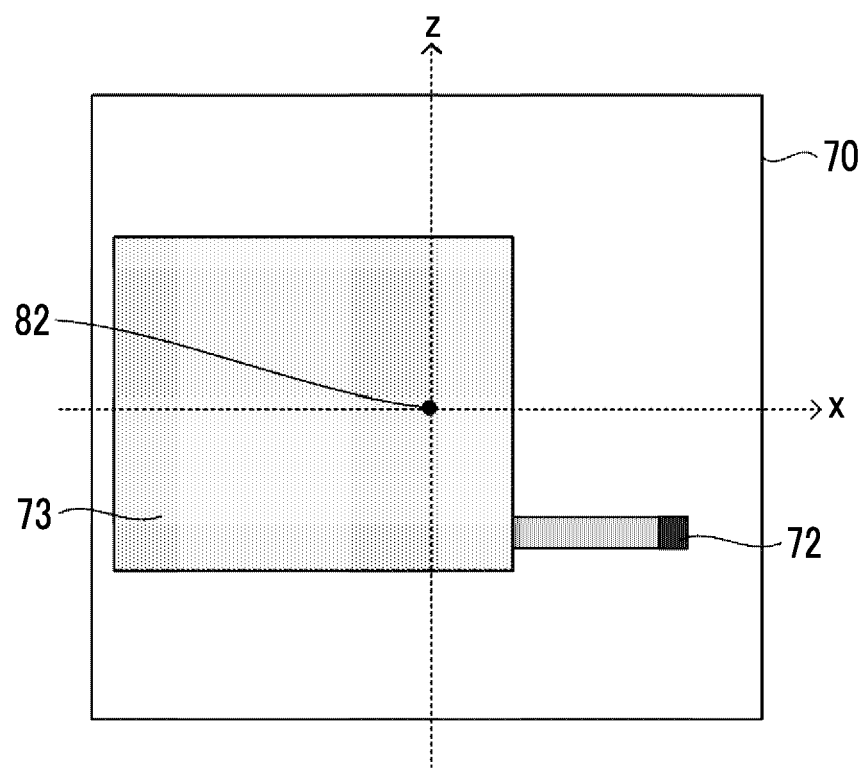
FIG. 9 is a diagram illustrating a modification example of the embodiment.

Further, for example, as in the example illustrated in FIG. 9, in a case in which a distance image 70 is obtained by imaging the radiation detector 30 or the detection surface 30A of the radiation detector 30 corresponding to the disposition of the radiation detector 30, the positional relationship between the marker 38 and the radiation detector 30 may be derived from the distance image 70. Specifically, it is assumed that, in the polar coordinate system described in the first embodiment, the positional relationship between the marker 38 and the TOF camera 14 is $(x_m, y_m, z_m)$, and the positional relationship between the radiation detector 30 and the TOF camera 14 is $(x_p, y_p, z_p)$. These positional relationships are obtained from a marker image 72 and a detector image 73 of the radiation detector 30 in the distance image. The positional relationship $(x_3, y_3, z_3)$ between the marker 38 and the radiation detector 30 is obtained by the following Expression (6).

$$(X_3, y_3, z_3) = (x_p, y_p, z_p) - (x_m, y_m, z_m) \quad (6)$$

Furthermore, in each of the above-described embodiments, the aspect in which the distance image is captured by the TOF method using the TOF camera has been described as an example of the aspect of capturing the distance image. However, the distance image capture device for capturing the distance image is not limited to the TOF camera. For example, the following aspect may be used: a distance image capture device that irradiates an object to be imaged with infrared light having a pattern and captures a distance image corresponding to reflected light from the object to be imaged is used, and a structured light method is applied to capture the distance image. Further, for example, a depth-from-defocus (DFD) method that restores the distance on the basis of the degree of blurring of an edge region included in the distance image may be applied. In the case of this aspect, for example, an aspect is known which uses a distance image captured by a monocular camera using a color aperture filter.

In addition, in each of the above-described embodiments, the aspect in which the TOF camera 14 or the visible light camera 15 is provided in the radiation emitting device 12 has been described. However, the position where the TOF camera 14 or the visible light camera 15 is provided is not limited to this aspect. The position of the TOF camera 14 or the visible light camera 15 is not limited, and the TOF camera 14 or the visible light camera 15 may be disposed at any position where the marker 38 can be imaged. The TOF camera 14 or the visible light camera 15 may be provided separately from the radiation emitting device 12.

Further, in each of the above-described embodiments, the aspect in which the console 10 is an example of the information processing device according to the present disclosure has been described. However, devices other than the console 10 may have the functions of the information processing device according to the present disclosure. In other words, for example, the radiation emitting device 12, the radiography apparatus 16, or an external device other than the console 10 may have some or all of the functions of the acquisition unit 60 and the derivation unit 62.

In each of the above-described embodiments, for example, the following various processors can be used as a hardware structure of processing units performing various processes such as the acquisition unit 60 and the derivation unit 62. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the SID derivation processing program 51 is stored (installed) in the storage unit 52 in advance has been described. However, the present disclosure is not limited thereto. The SID derivation processing program 51 may be recorded on a recording medium, such as a compact disc read only memory (CD-ROM), a digital versatile disc read only memory (DVD-ROM), or a universal serial bus (USB) memory, and then provided. In addition, the SID derivation processing program 51 may be downloaded from an external device through the network.

The disclosure of JP2020-064479 filed on Mar. 31, 2020 is incorporated herein by reference in its entirety.

All of the documents, the patent applications, and the technical standards described in the specification are incorporated by reference herein to the same extent as it is specifically and individually stated that individual documents, patent applications, and technical standards are incorporated by reference.

What is claimed is:

1. An information processing device comprising:
at least one processor; and
a memory that stores commands executable by the at least one processor, wherein the at least one processor acquires a captured image obtained by imaging a marker for measuring a distance between a radiation source and a radiation detector as an object to be imaged using an imaging device, derives a marker distance between the imaging device and the marker from an image of a marker region corresponding to the marker in the acquired captured image, and derives the distance between the radiation source and the radiation detector on the basis of the derived marker distance and information indicating a positional relationship between the radiation detector and the marker, and wherein the at least one processor stores the derived distance between the radiation source and the radiation detector in a storage device and acquires the distance between the radiation source and the radiation detector from the storage device to derive the distance between the radiation source and the radiation detector, without deriving the marker distance, in a case in which a position of the marker region specified from the captured image is the same as a position of the marker region specified from a captured image acquired previously.

2. The information processing device according to claim 1, wherein the at least one processor derives the distance between the radiation source and the radiation detector further on the basis of information indicating a positional relationship between the imaging device and the radiation source.

3. The information processing device according to claim 1, wherein the object to be imaged includes a subject that is positioned between the radiation source and the radiation detector, and the at least one processor derives a subject distance between the imaging device and the subject from an image of a subject region corresponding to the subject in the acquired captured image and derives a body thickness of the subject on the basis of the derived subject distance and the distance between the radiation source and the radiation detector.

4. The information processing device according to claim 1, wherein the object to be imaged includes a subject that is positioned between the radiation source and the radiation detector, and the at least one processor derives a subject distance between the imaging device and the subject from an image of a subject region corresponding to the subject in the acquired captured image and derives a body thickness of the subject on the basis of the derived subject distance, the distance between the radiation source and the radiation detector, and a distance between the radiation detector and the subject.

5. The information processing device according to claim 1, wherein the imaging device is a distance image capture device that captures a distance image indicating a distance to the object to be imaged as the captured image, and the at least one processor derives a distance indicated by the image of the marker region corresponding to the marker in the distance image as the marker distance.

6. The information processing device according to claim 5, wherein the at least one processor specifies the marker region in the distance image on the basis of a shape of the marker.

7. The information processing device according to claim 5, wherein the at least one processor acquires a visible light image obtained by imaging the marker as the object to be imaged using a visible light image capture device that captures the visible light image of the object to be imaged and sets, as the marker region, a region of an image, which corresponds to a position of the marker specified by the image of the marker in the visible light image, in the distance image.

8. The information processing device according to claim 5, wherein the distance image capture device captures the distance image using a time-of-flight (TOF) method.

9. The information processing device according to claim 1, wherein the imaging device is a visible light image capture device that captures a visible light image of the object to be imaged as the captured image, and the at least one processor derives the marker distance on the basis of a size of the marker region in the visible light image and a reference size of the marker region associated with a reference value of the marker distance.

10. An information processing device comprising:

at least one processor; and a memory that stores commands executable by the at least one processor, wherein the at least one processor acquires a captured image obtained by imaging a marker for measuring a distance between a radiation source and a radiation detector as an object to be imaged using an imaging device, derives a marker distance between the imaging device and the marker from an image of a marker region corresponding to the marker in the acquired captured image, and derives the distance between the radiation source and the radiation detector on the basis of the derived marker distance and information indicating a positional relationship between the radiation detector and the marker, and wherein the at least one processor stores the derived distance between the radiation source and the radiation detector in a storage device and outputs information indicating a warning for a period until the marker distance is derived from the captured image in a case in which a position of the marker region specified from the captured image is different from a position of the marker region specified from a captured image acquired previously.

11. An information processing method executed by a computer, the information processing method comprising:

acquiring a captured image obtained by imaging a marker for measuring a distance between a radiation source and a radiation detector as an object to be imaged using an imaging device;

deriving a marker distance between the imaging device and the marker from an image of a marker region corresponding to the marker in the acquired captured image; and deriving the distance between the radiation source and the radiation detector on the basis of the derived marker distance and information indicating a positional relationship between the radiation detector and the marker, wherein the derived distance between the radiation source and the radiation detector is stored in a storage device and the distance between the radiation source and the radiation detector is acquired from the storage device to derive the distance between the radiation source and the radiation detector, without deriving the marker distance, in a case in which a position of the marker region specified from the captured image is the same as a position of the marker region specified from a captured image acquired previously.

12. A non-transitory computer-readable storage medium storing an information processing program that causes a computer to execute a process comprising:

acquiring a captured image obtained by imaging a marker for measuring a distance between a radiation source and a radiation detector as an object to be imaged using an imaging device;

deriving a marker distance between the imaging device and the marker from an image of a marker region corresponding to the marker in the acquired captured image; and deriving the distance between the radiation source and the radiation detector on the basis of the derived marker distance and information indicating a positional relationship between the radiation detector and the marker, wherein the derived distance between the radiation source and the radiation detector is stored in a storage device and the distance between the radiation source and the radiation detector is acquired from the storage device to derive the distance between the radiation source and the radiation detector, without deriving the marker distance, in a case in which a position of the marker region specified from the captured image is the same as a position of the marker region specified from a captured image acquired previously.

* * * * *